US011389607B2

(12) United States Patent
Richard et al.

(10) Patent No.: US 11,389,607 B2
(45) Date of Patent: Jul. 19, 2022

(54) VENTILATION APPARATUS FOR CARDIOPULMONARY RESUSCITATION WITH DISPLAY OF THE TREND IN $CO_2$

(71) Applicant: Air Liquide Medical Systems, Antony (FR)

(72) Inventors: Jean-Christophe Richard, Antony (FR); Marceau Rigollot, Montrouge (FR); Bilal Badat, Paris (FR)

(73) Assignee: Air Liquide Medical Systems S.A., Antony (FR)

( * ) Notice: Subject to any disclaimer, the term of this patent is extended or adjusted under 35 U.S.C. 154(b) by 833 days.

(21) Appl. No.: 16/192,200

(22) Filed: Nov. 15, 2018

(65) Prior Publication Data

US 2019/0209796 A1     Jul. 11, 2019

(30) Foreign Application Priority Data

Jan. 11, 2018   (FR) ...................................... 1850225

(51) Int. Cl.
*A61M 16/00*     (2006.01)
*A61M 16/04*     (2006.01)
(Continued)

(52) U.S. Cl.
CPC ......... *A61M 16/024* (2017.08); *A61B 5/0836* (2013.01); *A61H 31/00* (2013.01);
(Continued)

(58) Field of Classification Search
CPC .............. A61M 16/021; A61M 16/022; A61M 16/024; A61M 16/026; A61M 16/066;
(Continued)

(56) References Cited

U.S. PATENT DOCUMENTS

2012/0016279 A1   1/2012   Banville et al.
2012/0145152 A1*   6/2012   Lain .......................... A61B 5/08
                                                         128/204.23
(Continued)

FOREIGN PATENT DOCUMENTS

AU    2015 202627    12/2015
EP    2 102 504    11/2007
(Continued)

OTHER PUBLICATIONS

English Machine Translation of WO-2016174324-A1 provided by Espacenet (Year: 2016).*
French Search Report and Written Opinion for corresponding FR 1850225, dated Aug. 31, 2018.
French Search Report and Written Opinion for related FR 1850224, dated Aug. 31, 2018.

*Primary Examiner* — Joseph D. Boecker
*Assistant Examiner* — Brian T Khong
(74) *Attorney, Agent, or Firm* — Allen E. White

(57) ABSTRACT

The invention relates to a respiratory assistance apparatus for delivering a respiratory gas, such as air, to a patient during cardiopulmonary resuscitation (CPR), having a source (1) of respiratory gas, means (4) for measuring the $CO_2$ content, and signal-processing and control means (5). The signal-processing and control means (5) are configured to process the $CO_2$ content measurement signals corresponding to measurements performed by the $CO_2$ content measurement means (4) during a given period of time (dt), and to calculate at least one mean $CO_2$ content value (Vmean) from the maximum $CO_2$ content values (Vmax) obtained over the time window (Ft), and to transmit said at least one mean $CO_2$ content value (Vmean) to the graphical user interface (7) which displays it.

13 Claims, 5 Drawing Sheets

(51) Int. Cl.
*A61B 5/083* (2006.01)
*A61M 16/10* (2006.01)
*A61H 31/00* (2006.01)
*A61M 16/08* (2006.01)

(52) U.S. Cl.
CPC ....... *A61H 31/005* (2013.01); *A61M 16/0051* (2013.01); *A61M 16/0066* (2013.01); *A61M 16/0069* (2014.02); *A61M 16/0402* (2014.02); A61H 2201/5089 (2013.01); A61H 2230/206 (2013.01); A61M 16/04 (2013.01); A61M 16/0833 (2014.02); A61M 2016/0027 (2013.01); A61M 2016/0033 (2013.01); A61M 2016/103 (2013.01); A61M 2202/0208 (2013.01); A61M 2205/05 (2013.01); A61M 2205/502 (2013.01); A61M 2205/8206 (2013.01); A61M 2230/432 (2013.01)

(58) Field of Classification Search
CPC .............. A61M 16/0069; A61M 16/04; A61M 16/0402; A61M 16/0404; A61M 16/0048; A61M 16/0051; A61M 16/0057; A61M 16/0066; A61M 2016/0413; A61M 2016/0027; A61M 2016/003; A61M 2016/0033; A61M 2016/103; A61B 5/0836; A61B 5/0833; A61B 5/085; A61B 5/087; A61B 5/0871; A61H 31/00; A61H 31/001; A61H 31/002; A61H 31/003; A61H 31/004; A61H 31/005; A61H 31/006; A61H 31/007; A61H 31/008
See application file for complete search history.

(56) References Cited

U.S. PATENT DOCUMENTS

| | | | |
|---|---|---|---|
| 2015/0238722 A1* | 8/2015 | Al-Ali | A61B 5/0836 |
| | | | 128/205.13 |
| 2015/0328417 A1 | 11/2015 | Lösser et al. | |
| 2016/0133160 A1 | 5/2016 | Packer et al. | |
| 2016/0256102 A1 | 9/2016 | Castiel et al. | |
| 2016/0287170 A1 | 10/2016 | Ronen et al. | |
| 2017/0368280 A1* | 12/2017 | Dermel | A61M 16/024 |
| 2018/0235510 A1 | 8/2018 | Orr et al. | |
| 2018/0325468 A1 | 11/2018 | Helfenbein | |

FOREIGN PATENT DOCUMENTS

| | | | |
|---|---|---|---|
| EP | 2 947 328 | 11/2015 | |
| EP | 2 986 856 | 2/2016 | |
| EP | 3 093 498 | 11/2016 | |
| EP | 2 954 213 | 2/2017 | |
| WO | WO 2008 059341 | 5/2008 | |
| WO | WO 2010 052608 | 5/2010 | |
| WO | WO 2012 114286 | 8/2012 | |
| WO | WO 2012 162048 | 11/2012 | |
| WO | WO 2014 045182 | 3/2014 | |
| WO | WO 2014 072981 | 5/2014 | |
| WO | WO 2014 122368 | 8/2014 | |
| WO | WO 2014 170571 | 10/2014 | |
| WO | WO-2016174324 A1 * | 11/2016 | ........... A61H 31/007 |
| WO | WO 2017 025869 | 2/2017 | |

* cited by examiner

VENTILATION APPARATUS FOR CARDIOPULMONARY RESUSCITATION WITH DISPLAY OF THE TREND IN $CO_2$

CROSS REFERENCE TO RELATED APPLICATIONS

This application claims the benefit of priority under 35 U.S.C. § 119 (a) and (b) to French Patent Application No. 1850225, filed Jan. 11, 2018, the entire contents of which are incorporated herein by reference.

BACKGROUND

The invention relates to a respiratory assistance apparatus, that is to say a medical ventilator, connected to a patient receiving cardiopulmonary resuscitation (CPR), that is to say a patient in cardiac arrest on whom cardiac massage is performed with alternating compression and decompression of the chest, with display of at least one mean $CO_2$ content value that is obtained, over a given time window, from a plurality of successive maximum $CO_2$ content values.

Medical apparatuses for mechanical ventilation, also called respiratory assistance apparatuses or medical ventilators, are currently used to deliver respiratory gas, for example oxygen-enriched air or non-oxygen-enriched air, to certain patients suffering from respiratory problems.

The delivery of the respiratory gas to the patient is currently effected by means of a motorized and controlled micro-blower, as is described in particular by EP-A-3093498, EP-A-2947328, EP-A-2986856, EP-A-2954213 or EP-A-2102504.

It is known to monitor the gaseous compounds present in the gas administered to the patients, particularly in the gases exhaled by the patients, which gases contain $CO_2$ resulting from the pulmonary gas exchanges, that is to say $CO_2$ produced by the patient's metabolism, conveyed to the lungs by the blood stream, then discharged during exhalation by the patient. Thus, $etCO_2$, standing for End Tidal $CO_2$ or $CO_2$ at the end of exhalation, corresponds to the measurement of the $CO_2$ fraction at the end of exhalation in the gases collected during the exhalation of an individual, whether the inhalation is natural or assisted, that is to say obtained by mechanical ventilation.

During mechanical ventilation, different techniques permit spectrophotometric analysis of the $CO_2$ fraction of the exhaled gases. To do this, the gas present in the exhalation circuit may be:
  either aspirated and then analysed by an analysis cell at a site remote from the respiratory circuit (this procedure is referred to as "sidestream" monitoring),
  or analysed near the patient, preferably at a Y-shaped piece arranged in the respiratory circuit in proximity to the patient (this procedure is referred to as "mainstream" monitoring).

During cardiopulmonary resuscitation (CPR) performed on a person in cardiorespiratory arrest, the alveolar $CO_2$ depends on the quantity of $CO_2$ generated by the cell metabolism, the cardiac output and the pulmonary ventilation/perfusion ratios. In theory, the more effective the CPR, the more the cell metabolism is preserved, and the cardiac output generated by the chest compressions is greater, the larger the quantity of CO2 returned to the lungs. For these reasons, the monitoring of etCO2 is recommended for conducting cardiopulmonary resuscitation (CPR).

FIG. 1 is a capnogram, which is a graphical representation of the variations of the $CO_2$ content in the respiratory gases of a patient over time (in seconds). This type of capnogram is seen in patients who are ventilated in situations where there is no cardiac arrest. As will be seen, it is divided into four successive phases:
  Phase I: This shows the inspiratory baseline, which must be stable at zero.
  Phase II: This is the ascending part of the capnogram and corresponds to the appearance of $CO_2$ in the gases that are exhaled, at the start of the exhalation of the patient, by emptying of the best ventilated alveoli. In reality, the exhalation begins slightly before this phase, since the gas exhaled at the start of exhalation is devoid of $CO_2$ because it has not participated in the gaseous exchanges, on account of the instrumental and anatomical dead spaces. The increase in $CO_2$ is all the slower as the lung is non-homogeneous and the alveoli have long time constants.
  Phase III: This corresponds to the alveolar plateau phase which corresponds to the gas rich in $CO_2$ originating from the least well ventilated alveoli. The maximum value at the plateau end (PetCO2) corresponds to the $etCO_2$ value.
  Phase IV: This corresponds to the decrease in the $CO_2$ concentration, caused by the onset of spontaneous or assisted (i.e. mechanical) ventilation.

However, during cardiopulmonary resuscitation (CPR) on a patient in cardiac arrest, the capnogram is very different for several reasons, notably:
  the chest compressions (CC) generate movements of small volumes of gas. These volumes, near the instrumental and anatomical dead space, disturb the capnogram between two ventilatory cycles as a result of a $CO_2$ lavage effect. Oscillating lines are therefore often observed, since the maximum $CO_2$ value on each chest compression does not cease to vary.
  the dynamic behaviour of opening and closing of the small airways during CPR has recently been reported during CPR. This phenomenon compromises the movements of exhaled gases and therefore the interpretation of the $CO_2$ concentrations during CPR.

It will thus be appreciated that $etCO_2$ as currently measured, that is to say during each chest compression, does not permit a reliable approximation of the alveolar $CO_2$ content.

Now, this alveolar $CO_2$ content is important for the medical personnel since it is a reflection of the quality of the CPR and of a possible resumption of spontaneous cardiac activity (RSCA).

Indeed, during CPR, the $CO_2$ concentration value or the trend in $CO_2$ is used by the first responder performing the cardiac massage, i.e. physician or any other medical personnel, as a "picture" of the blood flow and therefore of the efficacy of the cardiac massage being performed, the trend in $CO_2$ being defined as a graphical representation of several $CO_2$ concentration values measured successively over a given time window, for example during the 30 seconds to 5 minutes that have elapsed.

The recurring problem that results from this is that a measurement of the $CO_2$ content that does not take account of all or some of these factors, in particular the impact of the ventilation performed on the patient in cardiac arrest, makes the diagnostic use of this $CO_2$ measurement somewhat unreliable or even completely unreliable.

The current solutions involving the monitoring of $etCO_2$ are adapted to the $CO_2$ variations produced by breathing, whether mechanical or spontaneous. The frequencies involved are of the order of 10 to 30 c/min. The algorithms and mechanisms used are adapted to these frequencies and to small variations of the $CO_2$ between two respirations of the patient.

Now, during cardiopulmonary resuscitation, the frequencies of the chest compressions (CC) are of the order of 100 c/min, the volumes of gas that are mobilized are small, and the gas flow rates are considerable and irregular.

Under these conditions, the value of the $etCO_2$ varying at each chest compression, which is displayed on the graphical interface of the current ventilators, is refreshed at an inadequate frequency, since the ventilators attempt to follow the evolution of the $CO_2$ at the massage frequency, i.e. 100 c/min.

In other words, the value of the $etCO_2$ or the trend in $CO_2$ displayed by the current ventilators is not representative of a $CO_2$ concentration linked to the patient's metabolism, since the origin of the gas analysed is not guaranteed.

The documents WO-A-2014/072981, US-A-2016/133160 and US-A-2012/016279 propose methods for monitoring the $CO_2$ content in the gases exhaled by a patient receiving CPR, in which methods the ventilators indicate that the first responder must stop the cardiac massage when the $etCO_2$ content is greater than 30 mmHg, for example.

The problem addressed is therefore to make available a respiratory assistance apparatus, that is to say an improved medical ventilator, with which it is possible, during CPR, to display a reliable $CO_2$ value, that is to say a value that best reflects the alveolar $CO_2$ and its development over time, with the objective of better assisting the first responder during the CPR by providing him or her with pertinent information that facilitates monitoring of the CPR and by permitting or facilitating detection of the resumption of spontaneous cardiac activity, for example.

SUMMARY

The solution of the invention is therefore a respiratory assistance apparatus, that is to say a medical ventilator, for delivering a respiratory gas, such as air, to a patient during cardiopulmonary resuscitation (CPR), comprising:
- a source of respiratory gas for delivering a respiratory gas to said patient during cardiopulmonary resuscitation (CPR),
- means for measuring the $CO_2$ content in order to perform measurements of the concentration of $CO_2$ produced by said patient, and to supply $CO_2$ content measurement signals to signal-processing and control means,
- signal-processing and control means configured to process the $CO_2$ content measurement signals originating from the $CO_2$ content measurement means, and
- at least one graphical user interface or GUI, characterized in that:
- the signal-processing and control means are configured:
  a) to process the $CO_2$ content measurement signals corresponding to measurements performed by the $CO_2$ content measurement means during a given time period (dt), and to extract therefrom a plurality of $CO_2$ content values,
  b) to select the maximum $CO_2$ content value (Vmax) from said plurality of $CO_2$ content values measured during said given time period (dt),
  c) to repeat steps a) and b) in order to obtain several successive maximum $CO_2$ content values (Vmax) measured during a time window (Ft) comprising several successive time periods (dt),
  d) to calculate at least one mean $CO_2$ content value (Vmean) from the maximum $CO_2$ content values (Vmax) obtained over the time window (Ft), and
  e) to transmit said at least one mean $CO_2$ content value (Vmean) to the graphical user interface or GUI,
- and the graphical user interface is configured to display said at least one mean $CO_2$ content value (Vmean).

Depending on the case, the respiratory assistance apparatus of the invention may comprise one or more of the following technical features:
- the GUI is configured to display at least one $CO_2$ content value supplied by the signal-processing and control means.
- the GUI is configured to display said at least one mean $CO_2$ content value (Vmean) in the form of a numerical value or of a graphical representation, preferably a graphical representation, for example a curve, bar graph or other.
- the GUI is configured to display the most recent mean $CO_2$ content value (Vmean), that is to say the last value calculated over a given time window (Ft), in particular a sliding time window (Ft).
- the GUI is additionally configured to display the most recent maximum $CO_2$ content value (Vmax), that is to say the last maximum $CO_2$ content value determined during the last time period (dt) of a given time window (Ft) including several successive time periods (dt), in particular a sliding time window (Ft).
- the $CO_2$ produced by the patient. This $CO_2$ is observed during the exhalation of the patient, that is to say especially in the gases exhaled, or re-inhaled at the following inhalation in the case of gas trapped in part of the respiratory circuit, for example between a junction piece arranged upstream from the respiratory interface, such as a Y-shaped piece, and the $CO_2$ sensor.
- according to one embodiment, the GUI is configured to display at least some of the successive calculated mean $CO_2$ content values (Vmean) in the form of a curve composed of a succession of graphical symbols, each graphical symbol corresponding to a mean $CO_2$ content value (Vmean), in particular a trend curve.
- each mean $CO_2$ content value (Vmean) is displayed by the GUI in the form of a graphical symbol such as a dot, cross or any other symbol.
- according to another embodiment, the GUI is configured to display at least some of the successive calculated mean $CO_2$ content values (Vmean) in the form of a bar graph comprising several bars, each bar of said bar graph corresponding to a mean $CO_2$ content value (Vmean).
- preferably, the graphical display, in particular the trend curve or other, representing the variations of the mean $CO_2$ content value (Vmean) is refreshed, that is to say updated, after a regular and cyclical time interval, for example after a few seconds.
- the signal-processing and control means are configured to repeat steps a) to e) in such a way as to obtain several successive mean $CO_2$ content values (Vmean) calculated on the basis of maximum $CO_2$ content values (Vmax) obtained over successive time windows (Ft), in particular a sliding time window.
- the successive time windows (Ft) are advantageously a sliding time window.
- the time window (Ft) is between 20 seconds and 10 minutes, preferably between 30 seconds and 5 minutes, preferably at least 1 minute.

- the GUI is configured to display a trend curve composed of a succession of graphical symbols, each succession of graphical symbols corresponding to a mean $CO_2$ content value (Vmean). In other words, the GUI displays a time graph showing a graphical representation of each mean $CO_2$ content value (Vmean), namely a graphical symbol such as a dot or cross for example, as a function of the time (in seconds or minutes). This display is provided over a sliding time window of 30 seconds to 5 minutes for example, in particular of 1 to 3 minutes.
- the source of respiratory gas is an air source, in particular a motorized micro-blower, also called a turbine or compressor.
- the signal-processing and control means comprise at least one electronic board.
- the signal-processing and control means comprise at least one microprocessor, preferably a microcontroller.
- the microprocessor uses at least one algorithm.
- the means for measuring the $CO_2$ content are preferably arranged on the main flow of gas, i.e. in the mainstream.
- alternatively, the means for measuring the $CO_2$ content are arranged in the ventilator, i.e. in a sidestream, the one or more gas samples being withdrawn from the mainstream and then analysed in order to determine the $CO_2$ content.
- the source of respiratory gas is in fluidic communication with a gas conduit through which the respiratory gas is conveyed to the patient, i.e. as far as a respiratory interface.
- the gas conduit is in fluidic communication with a respiratory interface in such a way as to supply said interface with gas originating from the micro-blower.
- the means for measuring the $CO_2$ content are connected electrically to the signal-processing and control means.
- the means for measuring the $CO_2$ content are arranged in such a way as to perform $CO_2$ concentration measurements downstream from the gas conduit, preferably at a downstream end of the gas conduit.
- the means for measuring the $CO_2$ content are arranged upstream from and in immediate proximity to the respiratory interface, that is to say near the patient's mouth.
- the means for measuring the $CO_2$ content are arranged on a junction piece arranged between the respiratory interface and the gas conduit.
- the means for measuring the $CO_2$ content are arranged on a junction piece arranged between the respiratory interface and a Y-shaped piece comprising internal passages for gas.
- the respiratory interface is an endotracheal intubation tube, a face mask or a laryngeal mask, also called a supraglottic device, or any device suitable for administering gas.
- the respiratory interface is preferably an endotracheal intubation tube, commonly called a "tracheal tube".
- according to a first embodiment, the means for measuring the $CO_2$ content are arranged on a junction piece arranged upstream from the respiratory interface, preferably between the respiratory interface and the downstream end of the gas conduit, in particular between the respiratory interface and a Y-shaped piece comprising internal passages for gas.
- preferably, the means for measuring the $CO_2$ content are arranged on a junction piece comprising an internal passage for gas.
- according to a second embodiment, the means for measuring the $CO_2$ content are arranged in the apparatus, that is to say in the framework of the apparatus, and are connected, via a gas sampling conduit or similar, to a gas sampling site situated upstream from and in immediate proximity to the respiratory interface.
- in particular, the means for measuring the $CO_2$ content are connected fluidically to a gas sampling site carried by a junction piece, in particular arranged between the respiratory interface and the gas conduit, typically between the respiratory interface and a downstream end of said gas conduit.
- the junction piece is attached fluidically between the intermediate attachment piece, that is to say a Y-shaped piece, and the respiratory interface.
- it comprises a patient circuit comprising an inhalation branch through which gas can be conveyed to the patient, and an exhalation branch through which the gas exhaled by the patient can be discharged.
- the inhalation branch, the exhalation branch and the respiratory interface are connected mechanically and/or fluidically, directly or indirectly, to an intermediate attachment piece, in particular a Y-shaped piece.
- the gas conduit forms all or part of the inhalation branch of the gas circuit.
- the exhalation branch communicates fluidically with the atmosphere in order to discharge the gas exhaled by the patient, in particular a gas rich in $CO_2$.
- the inhalation branch and/or the exhalation branch comprise flexible hoses.
- preferably, all or part of the gas conduit forming all or part of the inhalation branch of the gas circuit is a flexible hose.
- the means for measuring the $CO_2$ content are arranged in such a way as to perform $CO_2$ concentration measurements in or at the outlet of the inhalation branch of the gas circuit.
- the signal-processing and control means are configured to control the source of respiratory gas and to deliver the respiratory gas in successive ventilatory cycles, in particular ventilatory cycles comprising two pressure levels.
- the given time period (dt) is of several seconds.
- each ventilatory cycle comprises a phase LP ($D_{LP}$) during which the gas is delivered by the micro-blower at a low pressure (LP), and a phase HP ($D_{HP}$) during which the gas is delivered by the micro-blower at a high pressure (HP), with HP>LP.
- the micro-blower is controlled to deliver gas at a low pressure (LP) of between 0 and 20 cm of water, preferably between 0 and 15 cm of water, more preferably between 0 and 10 cm of water.
- the micro-blower is controlled to deliver gas at a high pressure (HP) of between 5 and 60 cm of water, preferably between 5 and 45 cm of water, more preferably between 5 and 30 cm of water (with HP>LP).
- the phase LP has a duration longer than the phase HP.
- the phase LP has a duration of between 2 and 10 seconds, typically of the order of 3 to 6 seconds.
- the phase HP has a duration of between 0.5 and 3 seconds, typically of the order of 1 to 2 seconds.
- the given time period (dt) is of several seconds.
- the time period (dt) is between 2 and 10 seconds, typically of the order of 3 to 6 seconds.
- the time period (dt) corresponds to the duration of the phase LP of each ventilatory cycle.

the total duration of a ventilatory cycle is between 3 and 12 seconds.

the given time period (dt) encompasses several durations of successive chest compression and relaxation, typically between 5 and 20 chest compressions.

the means for measuring the $CO_2$ content are configured to perform measurements continuously.

the means for measuring the $CO_2$ content comprise a $CO_2$ sensor.

the means for measuring the $CO_2$ content comprise a capnometer as the $CO_2$ sensor.

the means for measuring the $CO_2$ content comprise a $CO_2$ sensor whose measuring tap is in fluidic communication with the interior or lumen of the junction piece arranged upstream from the respiratory interface.

it comprises storage means cooperating with the signal-processing and control means in order to store the plurality of $CO_2$ content values measured during the given time period.

it comprises storage means cooperating with the signal-processing and control means in order to store maximum values (Vmax) and/or mean values (Vmean) of the $CO_2$ content.

the storage means comprise a flash memory or hard disk memory.

it additionally comprises means for measuring the gas flow rate, which are configured to perform at least one measurement, preferably continuously, of the flow rate of the gas exhaled and the flow rate of gas inhaled by the patient. The flow rate permits monitoring of the chest compressions, and also the calculation and monitoring of the volumes of gas that are delivered and exhaled (ventilator and chest compressions).

the means for measuring the flow rate of gas comprise a flow rate sensor.

the graphical user interface (GUI) comprises a digital screen, preferably a touch screen.

the screen comprises several touch controls that activate different functions and/or several display zones or windows.

the screen is of the type with colour display.

it comprises a source of electric current, for example a battery or similar, preferably a rechargeable battery.

it comprises alarm means which are configured to trigger when the maximum value (Vmax) or mean value (Vmean) of the $CO_2$ content exceeds a threshold value.

the alarm means comprise an acoustic or visual alarm, or both.

the alarm means are programmed to trigger when the maximum value (Vmax) of $CO_2$ measured at a time t is such that: $[VmaxCO_2] > n \times [MeanCO_2]$, where:

n is between 1.20 and 2, preferably between 1.25 and 1.7, for example of the order of 1.5, $[VmaxCO_2]$ is the maximum $CO_2$ content value measured during a given duration dt, for example over a duration dt of between 2 and 10 seconds, $[MeanCO_2]$ is the mean value of the maximum $CO_2$ content values $[VmaxCO_2]$ determined for several successive durations dt in a given time window (FT) (FT > x.dt with x ≥ 2), for example a period of 30 seconds to 5 minutes, or more.

it comprises a rigid framework comprising the source of respiratory gas, the signal-processing and control means, the source of electric current and the storage means.

the GUI is arranged, particularly recessed, in one of the walls forming the framework of the ventilator.

the rigid framework is formed wholly or partly of polymer.

the means for measuring the $CO_2$ content are configured to perform successive measurements of $CO_2$ concentration over successive time periods (dt), that is to say time periods (dt) spaced apart from one another.

the means for measuring the $CO_2$ content are configured to perform successive measurements of $CO_2$ concentration over successive time periods (dt) during successive ventilatory cycles, in particular during the LP phases of successive ventilatory cycles.

The invention also relates to a method for monitoring cardiopulmonary resuscitation (CPR) performed on a patient in cardiac arrest, in which method:

use is made of a respiratory assistance apparatus comprising a source of respiratory gas, such as a microblower, in order to deliver a respiratory gas to a patient during cardiopulmonary resuscitation (CPR), measurements of the concentration of $CO_2$ produced by said patient are performed, for example by means of a capnometer, the $CO_2$ content measurement signals are processed, for example by signal-processing and control means such as a microprocessor, a plurality of $CO_2$ content values measured during a given time period (dt) are determined, the maximum $CO_2$ content value (Vmax) is selected from the plurality of $CO_2$ content values, the preceding steps are repeated in order to obtain several successive maximum $CO_2$ content values (Vmax) measured over a time window (Ft) comprising several successive time periods (dt), at least one mean $CO_2$ content value (Vmean) is calculated from the maximum $CO_2$ content values (Vmax) obtained over the time window (Ft), and said at least one mean $CO_2$ content value (Vmean) is displayed on a GUI.

BRIEF DESCRIPTION OF THE DRAWINGS

The invention will now be better understood from the following detailed description given as a non-limiting example and with reference to the appended figures, in which.

DESCRIPTION OF PREFERRED EMBODIMENTS

Figure 6:
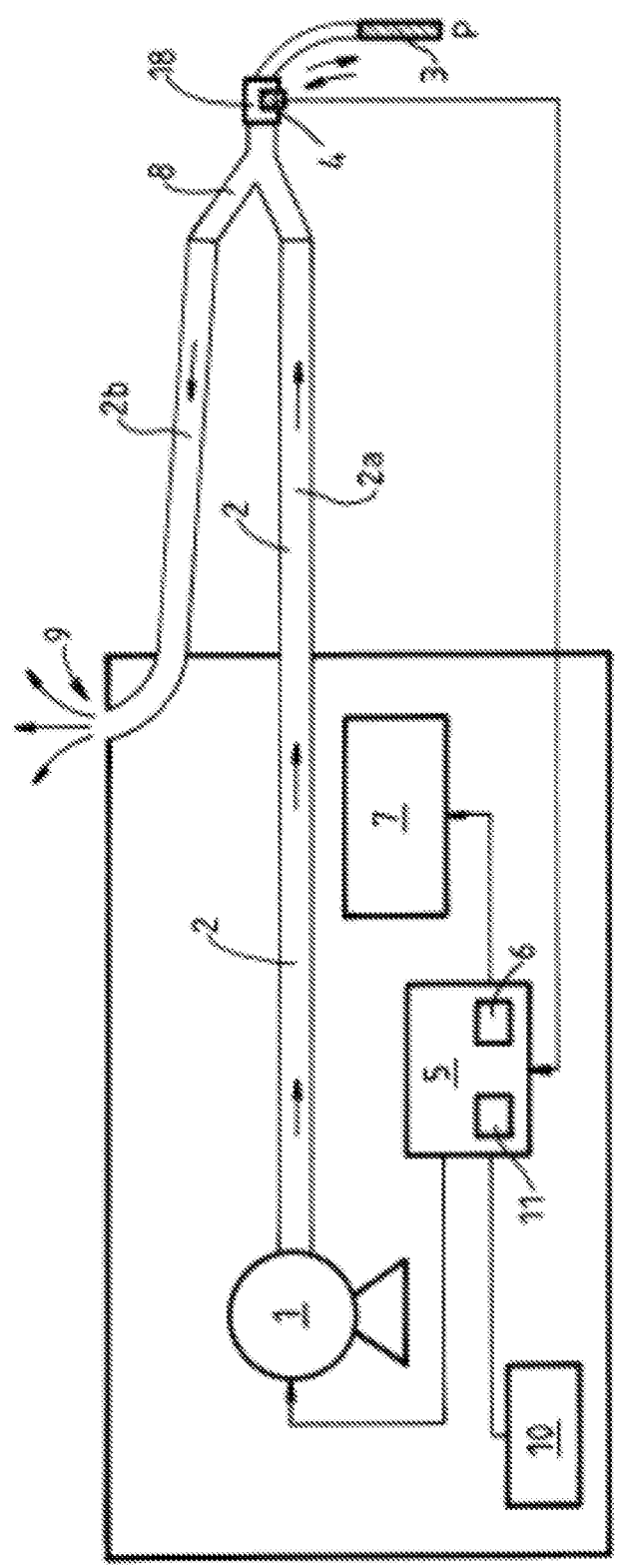
FIG. 6 is a diagram showing an embodiment of a respiratory assistance apparatus for CPR according to the invention.

FIG. 6 is a schematic representation of an embodiment of a respiratory assistance apparatus or medical ventilator according to the invention used for delivering a respiratory gas, typically air or oxygen-enriched air, to a patient P during cardiopulmonary resuscitation (CPR), that is to say to a person who is in cardiac arrest and on whom a first responder performs cardiac massage, with an alternation of chest compressions (CC) and relaxations (Re).

The apparatus comprises a source 1 of respiratory gas, such as a motorized micro-blower, which is in fluidic communication with a gas conduit 2 of the inhalation branch 2a of the patient circuit 2a, 2b in order to deliver the respiratory gas to said patient P during the CPR.

The source 1 of respiratory gas is governed, that is to say controlled, by signal-processing and control means 5, in particular an electronic board with microprocessor 6 or similar. The signal-processing and control means 5 control the source 1 of respiratory gas in such a way that it delivers the gas in accordance with one or more predefined ventilation modes.

It preferably makes it possible to control the source 1 of respiratory gas so as to deliver the gas in accordance with a "normal" ventilatory mode, corresponding to ventilation of a patient who is not in cardiac arrest, and a "CPR" ventilatory mode, corresponding to ventilation of a patient who is in cardiac arrest and on whom a first responder initiates or performs CPR.

Figure 2:
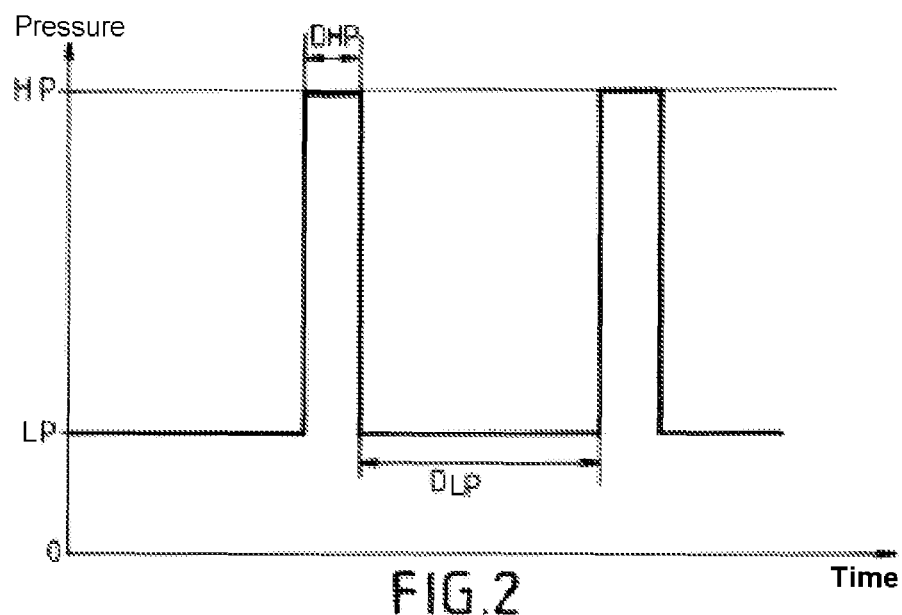
FIG. 2 is a diagram showing a ventilatory cycle with two pressure levels that can be used by the apparatus of FIG. 6 in order to ventilate a patient in cardiopulmonary arrest during CPR.

For example, in accordance with a ventilation mode intended for CPR, the source 1 of respiratory gas is controlled so as to deliver the respiratory gas, typically air, in a ventilatory cycle comprising several pressure levels or of the BiPAP type, as illustrated in FIG. 2, in particular two pressure levels comprising a low pressure level, for example a low pressure (LP) of between approximately 0 cm $H_2O$ and 15 cm $H_2O$, and a high pressure level, for example a high pressure (HP) of between approximately 7 cm $H_2O$ and 40 cm $H_2O$.

The gas is delivered alternately between these two pressure levels (LP, HP), as is illustrated in FIG. 2, throughout the CPR performed by the first responder, that is to say while the first responder performs the chest compressions and relaxations. The duration ($D_{LP}$) of delivery of gas at low pressure (LP) by the micro-blower 1 is between 2 and 10 seconds, typically of the order of 3 to 6 seconds, whereas the duration ($D_{HP}$) of delivery of gas at high pressure (HP) is less than 3 seconds, for example of the order of 0.5 to 1.5 seconds.

Figure 3:
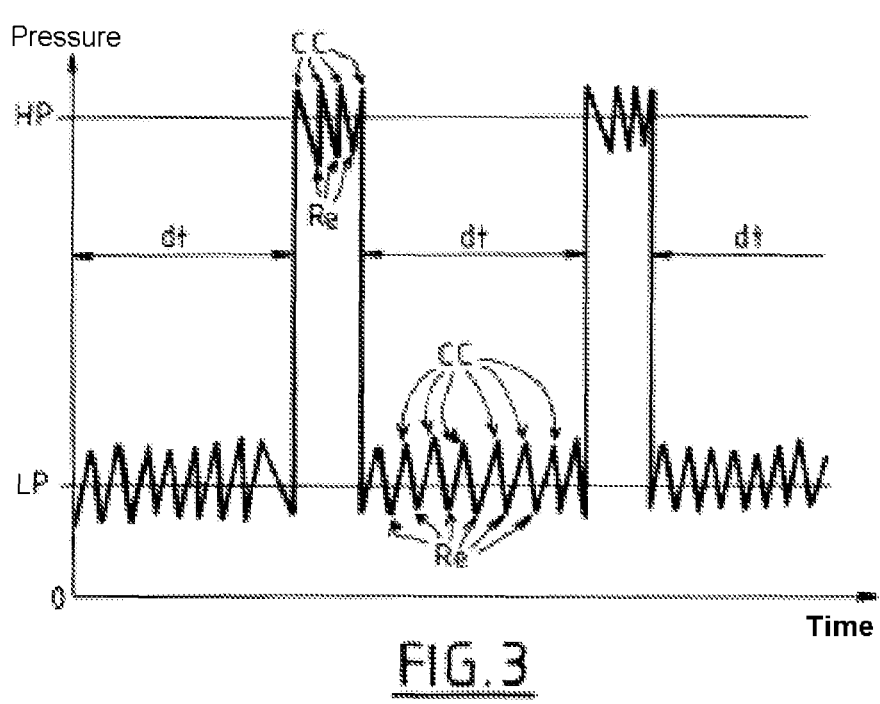
FIG. 3 illustrates the pulmonary pressure variations of a patient in cardiopulmonary arrest during CPR.

The chest compressions (CC) and relaxations (Re) resulting from the cardiac massage will themselves bring about pressure variations in the lungs of the patient, which will increase or decrease the pressure supplied by the micro-blower 1, and this will lead, in the patient's lungs, to a pressure curve as illustrated in FIG. 3 where the pressure peaks at the high plateaus (i.e. at HP) and low plateaus (i.e. at LP) reflect the chest compressions (CC) with increased pressure, since the chest yields under the pressure of the CC performed by the first responder, and the relaxations (Re) with low pressure, since the chest rises again in the absence of CC.

As will be seen from FIGS. 2 and 3, the given time period (dt), during which the plurality of $CO_2$ content values are measured and the maximum $CO_2$ content value (Vmax) is extracted therefrom, corresponds to the duration ($D_{LP}$) of delivery of gas at low pressure (LP), i.e. between 2 and 10 seconds, typically between 3 and 6 seconds.

The gas delivered by the micro-blower 1 is conveyed through the gas conduit 2 which forms all or part of the inhalation branch 2a of the patient circuit 2a, 2b. The respiratory gas, generally air, is delivered to the patient via a gas distribution interface, for example here an endotracheal intubation tube 3, more simply called a tracheal tube. However, other interfaces may be used, in particular a face mask or a laryngeal mask.

The gas conduit 2 of the inhalation branch 2a is in fluidic communication with the tracheal tube 3 in such a way as to supply the latter with the gas, such as air, originating from the source 1 of respiratory gas. The gas conduit 2 will in fact be attached to the tracheal tube 3 by way of an intermediate attachment piece, typically a Y-shaped piece 8 comprising internal passages for the gas. This Y-shaped intermediate attachment piece 8 comprises internal passages for gas.

The Y-shaped piece 8 is likewise attached to the exhalation branch 2b of the patient circuit 2a, 2b so as to be able to collect and convey the gases rich in $CO_2$ that are exhaled by the patient P and to discharge them to the atmosphere (at 9).

Also provided are means 4 for measuring the $CO_2$ content, called a $CO_2$ sensor or more simply a capnometer, which means are designed to perform measurements of the concentration of $CO_2$ in the gas exhaled by the patient P and to deliver the corresponding $CO_2$ content measurement signals to the signal-processing and control means 5, where these measurement signals can be processed by one or more calculation algorithms or similar.

In the embodiment in FIG. 6, the $CO_2$ sensor is arranged near the mouth of the patient P in the mainstream configuration, that is to say upstream from and in immediate proximity to the respiratory interface 3, preferably between the intermediate attachment piece 8, i.e. the Y-shaped piece, and the respiratory interface 3, i.e. the tracheal tube, for example on a junction piece 18 (cf. FIG. 6).

According to another embodiment (not shown), the $CO_2$ sensor can be arranged in the "sidestream" configuration. In this case, the $CO_2$ sensor 4 is situated in the framework of the respiratory assistance apparatus and is connected, via a gas sampling line, such as tubing or the like, to a gas sampling site situated upstream from and in immediate proximity to the respiratory interface 3, for example on the junction piece 18. This gas sampling line communicates fluidically with the lumen of the junction piece 18 in such a way as to be able to collect a sample of the gas from there and convey it then to the $CO_2$ sensor situated in the framework of the apparatus.

In all cases, the junction piece 18 comprises an internal passage for gas, allowing the gas to pass through it.

Preferably, the $CO_2$ sensor performs continuous measurements of the concentration of $CO_2$ in the gas flowing through the junction piece 18, which gas is enriched in $CO_2$ during its passage through the lungs of the patient P, where gaseous exchanges take place.

The $CO_2$ content measurement signals are then transmitted by the $CO_2$ sensor to the signal-processing and control means 5 by an electrical connection or similar, in particular by wire or similar.

The monitoring of the $CO_2$ content, in particular of the $etCO_2$ which indirectly reflects the alveolar $CO_2$ content, is in fact of great importance during CPR, especially for detecting a resumption of spontaneous cardiac activity (RSCA). This is because a resumption of spontaneous cardiac activity (RSCA), hence a significant increase of the cardiac output, brings about a rapid increase in the quantity of $CO_2$ carried by the blood to the lungs and transferred through the alveolar-capillary membrane, this $CO_2$ then being found again in the gas flow exhaled by the patient.

Figure 1:
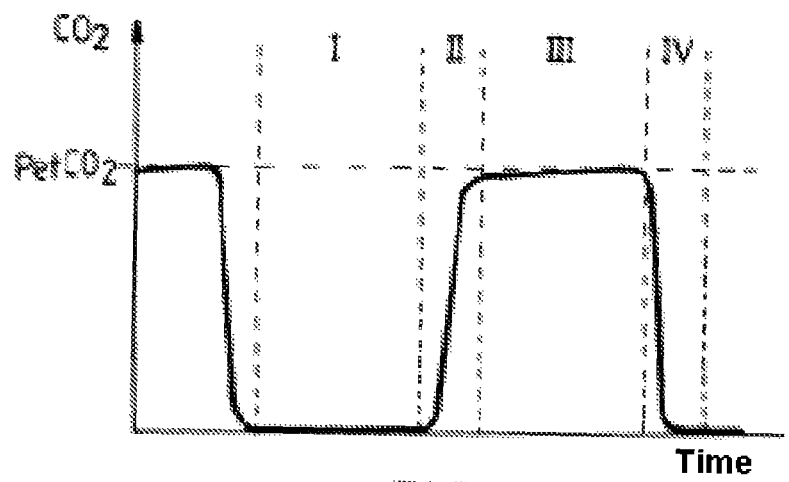
FIG. 1 is a graphical representation of the variations of the $CO_2$ content in the respiratory gases of a normal patient.
Figure 5:
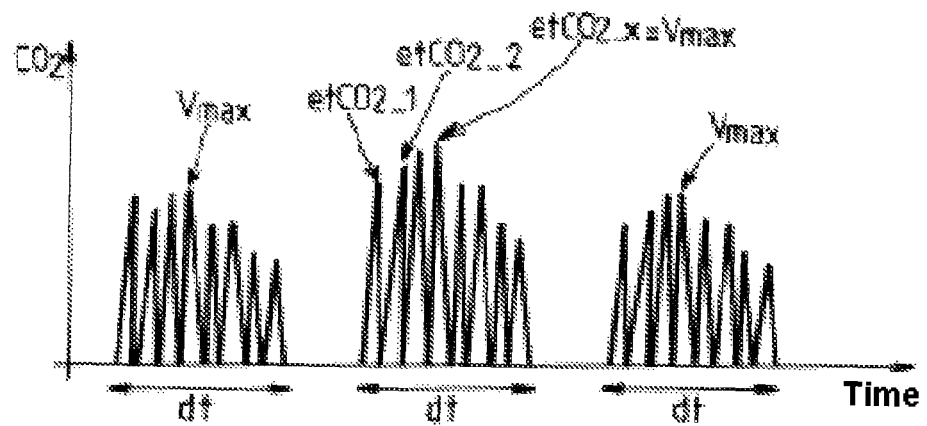
FIG. 5 is a diagram showing the $CO_2$ content peaks during the ventilatory cycles implemented during CPR.
Figure 7:
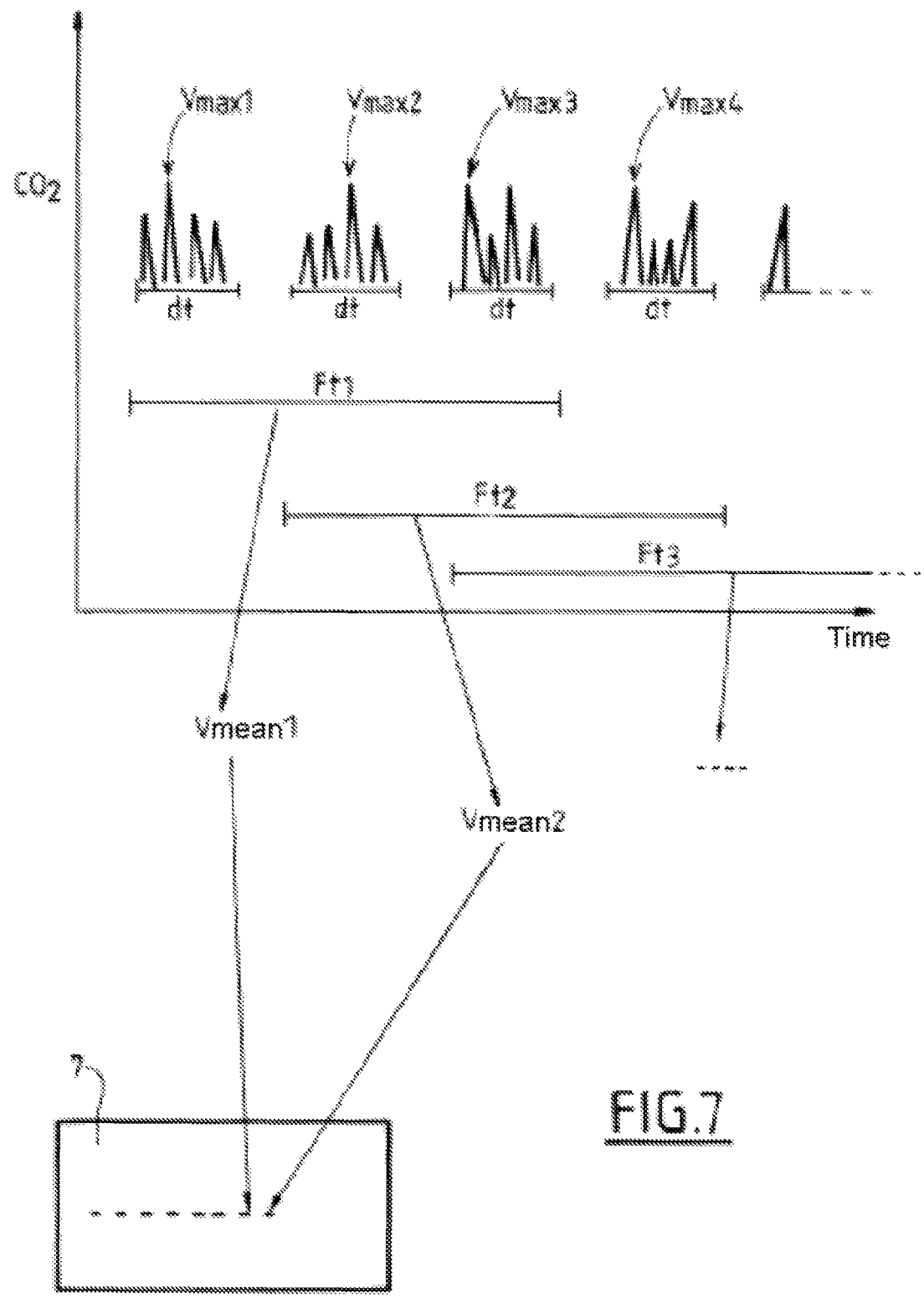
FIG. 7 is a diagram showing the measurements and time intervals used to calculate and display the trend in $CO_2$. Successive $CO_2$ content measurement time period (dt) are shown from which the Vmax1, Vmax 2, Vmax3 and Vma4 are selected. Sliding windows $Ft_1$, $Ft_2$ and $Ft_3$ corresponding to three dt's are shown, for which Vmean1 and Vmean 2 are calculated.

Hence, according to the present invention and as illustrated in FIG. 7, the signal-processing and control means 5, particularly the microprocessor 6, are configured:

a) to process the $CO_2$ content measurement signals corresponding to measurements performed by the $CO_2$ content measurement means 4, typically a capnometer, during a given time period (dt), for example between 1 and 7 seconds, and to extract therefrom a plurality of $CO_2$ content values. During the time period (dt) in question, the patient undergoes cardiac massage with a succession of chest compressions and relaxations, which causes gas to enter and leave the lungs, thus causing variations in the $CO_2$ contents of the gas flow exhaled, that is to say leaving the lungs under the effect of the chest compressions, especially as a function of the force applied by the first responder, which is not equal from one contraction to another, as is illustrated in FIGS. 3 and 5 for example.

b) to select the maximum $CO_2$ content value (Vmax) from said plurality of $CO_2$ content values measured during said given time period (dt). In other words, from the different $CO_2$ contents measured during the time period dt, one selects only the highest one which is the most representative of the $CO_2$ content, i.e. the et$CO_2$ content, during the time period (dt) in question. To do this, the signal-processing and control means 5 store and then compare the measured $CO_2$ values in order to retain only the highest one.

c) to repeat steps a) and b) in order to obtain several successive maximum $CO_2$ content values (Vmax) measured during a longer time window (Ft), for example between 30 seconds and 5 minutes, comprising several successive time periods (dt). In other words, the signal-processing and control means 5 perform measurements during several successive periods (dt) and select, for each of these, the maximum $CO_2$ content value over each of the desired periods obtained during the long time window including said successive periods (dt). All of these maximum $CO_2$ content values are stored by the storage means 11.

d) to calculate at least one mean $CO_2$ content value (Vmean) from the maximum $CO_2$ content values (Vmax) obtained over the time window (Ft). The maximum $CO_2$ content values (Vmax) which have been stored over the whole of the long time window (Ft) are retrieved from the storage means 11, and then a means $CO_2$ content value is calculated from these for the time window (Ft) in question.

e) to transmit said at least one mean $CO_2$ content value (Vmean) to the GUI 7, which then displays this means $CO_2$ content value in the form of a numerical value or a graphical representation, advantageously in the form of a graphical representation, namely a graphical symbol, for example a dot, a cross or any other symbol, which is displayed on a time graph showing the graphical representation of the mean $CO_2$ content value (Vmean) as a function of time.

f) steps a) to e) are repeated as many times as is necessary over successive time periods (dt) and over a sliding time window (Ft) of a duration of between typically 1 and 5 minutes, so as to obtain mean $CO_2$ content values (Vmean) over the course of time, thus making it possible to monitor the development of the content of $CO_2$ in the gas flows leaving the patient's lungs during the cardiac massage, in particular under the effect of the chest compressions. To put it another way, the GUI 7 displays, for example, a trend curve composed of a succession of graphical symbols. Of course, another graphical representation could be adopted, for example bar graphs or similar.

The medical ventilator of the invention permits a measurement, advantageously a continuous measurement, of the concentration of $CO_2$ in the gases exhaled by the patient P. The measurement is performed by the capnometer 4, which is arranged on the pathway of the gas, very close to the mouth of the patient P, preferably between the Y-shaped piece 8 and the respiratory interface 3, and the measurement signals are transmitted to the signal-processing and control means 5 via electrical lines or similar.

This measurement of the concentration of $CO_2$ in the gases exhaled by the patient P makes it possible to obtain a plurality of maximum $CO_2$ content values which are then processed by the signal-processing and control means 5 in order to calculate mean $CO_2$ content values from several successive maximum $CO_2$ content values obtained over a given time window comprising several successive given time periods during which the maximum $CO_2$ content values have been determined, preferably a sliding time window (cf. FIG. 7).

The mean $CO_2$ value (Vmean) is not necessarily updated when each point is displayed, and instead it can be refreshed and displayed after a defined duration, for example a few seconds.

The reason is that, as has already been explained, the $CO_2$ concentration value which best reflects the alveolar $CO_2$ content, and which hence gives a good indication of the state of the blood flow in the patient P during the CPR, is the highest $CO_2$ value, also called the maximum peak value, as illustrated in FIG. 5 which shows the development of the $CO_2$ content and of the etCO2 measurements for given durations (dt), in the context of CPR performed on a person in cardiac arrest.

More precisely, during CPR, the $CO_2$ content in the gas exhaled by the patient, on account of the cardiac massage performed, varies depending on the presence or absence of chest compressions (CC).

Thus, during the insufflation of air by the micro-blower 1 of the ventilator, then during the first compression(s) following this insufflation, no $CO_2$ is detected in the gas flow passing through the conduit 2 as far as the Y-shaped piece 8 and then to the tracheal tube 3, which thereafter distributes this air to the lungs of the patient P. After a few chest compressions (CC) performed by a first responder, $CO_2$ is detected at the Y-shaped piece 8 by the capnometer 4, since the alternating chest compressions (CC) and relaxations (Re) cause movements of air entering and leaving the lungs of the patient.

Exhaled air rich in $CO_2$ is then found again at the Y-shaped piece 8, and measurements of the concentrations of $CO_2$ can be carried out by the capnometer 4. The corresponding signals are sent to the signal-processing and control means 5, where they are processed in the way explained above.

The maximum $CO_2$ content value (Vmax) determined for the given durations (dt), for example durations of 3 to 7 seconds, is the value that best represents the alveolar$CO_2$. In fact, the $CO_2$ present at the Y-shaped piece 8 is "washed out" little by little on account of the successive and repeated chest compressions and tends to decrease after reaching this maximum value, since the chest compressions thus cause the discharge to the atmosphere (at 9) of the gases rich in $CO_2$, via the exhalation branch 2b of the patient circuit. The successive chest compressions thus generate different $CO_2$ levels, the most representative being the maximum peak value, as illustrated in FIG. 5 which shows the development of the $CO_2$ content in the gas and illustrates several measurements of the etCO$_2$ measured over several successive durations dt, for example durations of 3 to 6 seconds, while CPR is being performed. It will be seen here that the $CO_2$ content of the gas is not constant during a given time interval dt and that there is therefore necessarily a maximum $CO_2$ content value (Vmax) over each interval dt, that is to say the peak value.

The ventilator thus stores (at 11) all the peak values of $CO_2$ during each time period dt, typically between 3 and 7 seconds, and determines the maximum $CO_2$ content value (Vmax) from the plurality of peaks ($EtCO2_{-1}$, $EtCO2_{-2}$, $EtCO2_{-3}$, . . . , $EtCO2\_x$) measured over a given time period, as is illustrated in FIG. 5.

Figure 4:
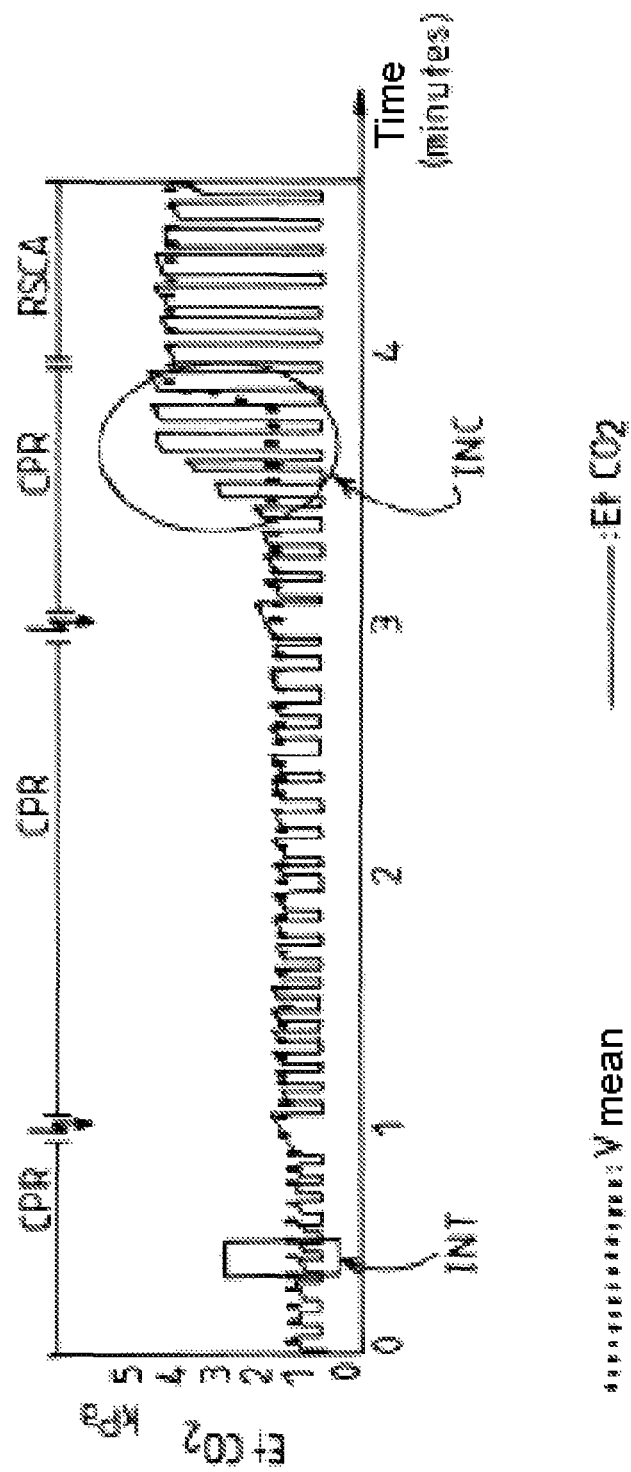
FIG. 4 is a diagram showing the quantity of $CO_2$ measured by the capnometer of the apparatus of FIG. 6 during CPR, at the moment of and after resumption of spontaneous cardiac activity (RSCA)

As is illustrated in FIG. 7, these operations are repeated over several successive given time periods (dt) comprised in a longer time window (Ft), for example a time window (Ft) of 30 seconds to 5 minutes, advantageously a sliding time window (Ft), so as to be able to determine and display on the GUI 7, preferably continuously, a plurality of mean $CO_2$ content values (Vmean) in the form of a graphical representation, preferably a trend curve over time, on which graphical symbols represent the different mean $CO_2$ content values (Vmean) as a function of time, as is illustrated in FIG. 4.

Furthermore, these maximum $CO_2$ content values (Vmax) are processed by the signal-processing and control means 5 so as to calculate a succession of mean $CO_2$ content values (Vmean) over a given time window comprising several successive given time periods during which said maximum $CO_2$ content values (Vmax) have been determined, preferably a sliding time window, for example a time window of between 30 seconds and 5 minutes.

The mean $CO_2$ content values (Vmean) thus determined are displayed on the GUI 7, likewise in the form of a graphical representation such as a curve, a bar graph or similar, preferably in the form of a trend curve on which the mean values (Vmean) are represented by a succession of symbols such as dots or similar (FIG. 4). In FIG. 4, the curve « . . . . . . » represents the Vmean values and the curve « _____ » represents the values of etCO$_2$.

The data calculated from this $CO_2$, in particular the Vmean values, constitute a useful indicator for the first responder, which allows him to control the CPR, since it reflects the state of the circulation and metabolism of the patient from the moment when the patient is intubated (INT) and CPR is performed (cf. FIG. 4). Indeed, the more effective the CPR, the greater the quantity of $CO_2$ produced and transferred through the alveolar-capillary membrane, hence the greater the quantity of $CO_2$ that can be detected at the capnometer 4.

Hence, in the case of a resumption of spontaneous cardiac activity (RSCA), the circulation recovers abruptly and therefore the quantity of alveolar $CO_2$ increases in parallel, which induces a substantial increase in the quantity of $CO_2$ detected by the capnometer 4 by a factor often greater than 2, as is illustrated in FIG. 4. It will in fact be seen from FIG. 4 that the etCO$_2$ is always below 2.5 during the CPR but that it increases (INC) suddenly to reach over 5 at the moment of resumption of spontaneous cardiac activity (RSCA), i.e. after approximately 3 to 4 minutes following the intubation (INT) of the patient and the start of CPR.

In the context of the invention, the fact that the GUI 7 displays a trend curved based on the mean values (Vmean) determined over a sliding time window (Ft) allows the first responder to better detect the occurrence of the spontaneous resumption of cardiac activity (SRCA) since the curve Vmean shows a strong increase (INC in FIG. 4) at the moment of a RSCA on account of increased release of $CO_2$ in the gases exhaled by the lungs.

Thus, when the first responder notes a strong rise (INC) of the curve showing the mean $CO_2$ content values (Vmean) on the GUI 7, he can conclude from this that the patient is at the start of RSCA and, for example, can decide to analyse the heart rate and, if appropriate, stop the cardiac massage.

The ventilator additionally permits parallel performance of a continuous measurement of the exhaled and inhaled gas flow rates, with the aid of a flow rate sensor (not shown).

Advantageously, the ventilator of the invention can also include alarm means designed and programmed to warn the first responder or the like when one or more of the measured maximum $CO_2$ content values exceeds or, conversely, drops below a given value that is predefined or calculated continuously.

In particular, an acoustic and/or visual alarm is provided which triggers when the maximum $CO_2$ content measured, at a time t, is greater than a threshold value, for example: $[VmaxCO_2] > 1.5 \times [MeanCO_2]$ where:

[VmaxCO$_2$] is the maximum $CO_2$ content value measured during a given duration dt, for example over a duration dt of between 2 and 10 seconds,

[MeanCO$_2$] is the mean value of the maximum $CO_2$ content values [VmaxCO$_2$] determined for several successive durations dt in a given time window (FT) (FT>x.dt with x≥2:2), for example a period of 30 seconds to 5 minutes, or more.

Similarly, the alarm can trigger in the event of the $CO_2$ concentration dropping abruptly below a given minimum value, which could be the sign of a new cardiac arrest of the patient, of hyperventilation, or of obstruction of the gas circuit between the patient and the machine, for example a flexible conduit that is bent or crushed and no longer allows the gas to pass through.

A source 10 of electric current, such as a rechargeable battery or similar, integrated in the framework of the ventilator, directly or indirectly supplies electric current to the signal-processing and control means 5, the micro-blower 1, the GUI 1 or any other element of the apparatus, in particular a storage memory 11.

Generally, the invention relates to a medical ventilator suitable for use during cardiopulmonary resuscitation (CPR), comprising a source 1 of respiratory gas, such as a micro-blower, means for measuring the $CO_2$ 4, such as a capnometer, signal-processing and control means 5 receiving and processing the $CO_2$ content measurement signals originating from the $CO_2$ measurement means 4, in order to obtain successive maximum $CO_2$ content values (Vmax) measured over a time window (Ft) and to calculate at least one mean $CO_2$ content value (Vmean) from the maximum $CO_2$ content values (Vmax) obtained over the time window (Ft), and a GUI 7 configured to display said at least one mean $CO_2$ content value (Vmean).

The respiratory assistance apparatus or medical ventilator according to the present invention is particularly suitable for use during cardiopulmonary resuscitation (CPR) on a person (i.e. a patient) in cardiopulmonary arrest, in the context of which a respiratory gas such as pressurized air is supplied, in accordance with a ventilatory cycle with several pressure levels, to said person undergoing the cardiac massage with alternating chest compressions and relaxations. To facilitate its transport by the first aid responders, for example by a physician, a nurse, a fire-fighter or similar, the ventilator of the invention is preferably arranged in a bag for carrying it.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A respiratory assistance apparatus for delivering a respiratory gas to a patient during cardiopulmonary resuscitation (CPR), comprising:
    a source (1) of the respiratory gas for delivering the respiratory gas to said patient during the cardiopulmonary resuscitation (CPR),
    a CO2 content measurement device (4) for measuring a $CO_2$ content produced by the patient, and to supply $CO_2$ content measurement signals to a signal-processing and control system (5),
    the signal-processing and control system (5) configured to process the $CO_2$ content measurement signals originating from the $CO_2$ content measurement device (4), and
    at least one graphical user interface (7),
characterized in that:
    the signal-processing and control system (5) is configured:
    a) to process the $CO_2$ content measurement signals corresponding to the measurements performed by the $CO_2$ content measurement device (4) during a given time period (dt), and to extract therefrom a plurality of end tidal $CO_2$ ($EtCO_2$) content values,
    b) to select a maximum $EtCO_2$ content value (Vmax) from said plurality of $EtCO_2$ content values measured during said given time period (dt),
    c) to repeat steps a) and b) in order to obtain several successive maximum $EtCO_2$ content values (Vmax) measured over a time window (Ft) comprising several successive time periods (dt),
    d) to calculate at least one mean $CO_2$ content value (Vmean) from only the several successive maximum $EtCO_2$ content values (Vmax) obtained over the time window (Ft), and
    e) to transmit said at least one mean $CO_2$ content value (Vmean) to the graphical user interface (7),
    and the graphical user interface (7) is configured to display said at least one mean $CO_2$ content value (Vmean).

2. The apparatus according to claim 1, characterized in that the signal-processing and control system (5) is configured to repeat the steps a) to e) in such a way as to obtain several successive mean $CO_2$ content values (Vmean) calculated based on the several successive maximum $EtCO_2$ content values (Vmax) obtained over successive time windows (Ft), preferably a sliding time window (Ft).

3. The apparatus according to claim 2, characterized in that the time window (Ft) is between 20 seconds and 10 minutes.

4. The apparatus according to claim 1, characterized in that the graphical user interface (7) is configured to display said at least one mean $CO_2$ content value (Vmean) in the form of a graphical representation or a numerical value.

5. The apparatus according to claim 1, characterized in that the graphical user interface (7) is configured to display at least some of the calculated successive mean $CO_2$ content values (Vmean) in the form:
    of a curve composed of a succession of graphical symbols, each graphical symbol corresponding to said at least one mean $CO_2$ content value (Vmean), or
    of a bar graph comprising several bars, each bar of said bar graph corresponding to a mean $CO_2$ content value (Vmean).

6. The apparatus according to claim 1, characterized in that the signal-processing and control system (5) comprises at least one microprocessor.

7. The apparatus according to claim 1, characterized in that the CO2 content measurement device (4) for measuring the $CO_2$ content comprises a capnometer.

8. The apparatus according to claim 1, characterized in that the source (1) of respiratory gas is in fluidic communication with a gas conduit (2), the gas conduit (2) being in fluidic communication with a respiratory interface (3).

9. The apparatus according to claim 8, characterized in that the CO2 content measurement device (4) for measuring the $CO_2$ content is arranged:
    either upstream from and in immediate proximity (18) to the respiratory interface (3),
    or in the apparatus, being connected to a gas sampling site (18) situated upstream from and in immediate proximity to the respiratory interface (3).

10. The apparatus according to claim 1, characterized in that the given time period (dt) is between 2 and 10 seconds.

11. The apparatus according to claim 1, characterized in that the CO2 content measurement device (4) for measuring the $CO_2$ content is configured to perform measurements continuously.

12. The apparatus according to claim 1, characterized in that the graphical user interface (GUI) comprises a digital screen.

13. The apparatus according to claim 1, characterized in that the signal-processing and control system (5) is configured to control the source (1) of respiratory gas and to deliver the respiratory gas in ventilatory cycles comprising two pressure levels, the source (1) of respiratory gas comprising a motorized micro-blower.

* * * * *